US012758918B2

(12) United States Patent
Zeng et al.

(10) Patent No.: US 12,758,918 B2

(45) Date of Patent: Oct. 13, 2026

(54) PHOTOCATALYTIC MATERIAL, METHOD FOR PREPARING THE PHOTOCATALYTIC MATERIAL AND PHOTOCATALYTIC AIR SCREEN FILTER FOR EPIDEMIC PREVENTION

(71) Applicants: Chongqing Institute of East China Normal University, Chongqing (CN); ROI Optoelectronics Technology CO, LTD., Shanghai (CN); Yunnan Huapu quantum Material Co., Ltd, Kunming (CN); GuangDong ROI Optoelectronics Technology Co., Ltd., Dongguan (CN); East China Normal University, Shanghai (CN); Chongqing Huapu Intelligent Equipment Co., Ltd., Chongqing (CN); Chongqing Huapu Quantum Technology Co., Ltd., Chongqing (CN)

(72) Inventors: Heping Zeng, Chongqing (CN); Mengyun Hu, Chongqing (CN)

(73) Assignees: Chongqing Institute of East China Normal University, Chongqing (CN); ROI Optoelectronics Technology CO, LTD., Shanghai (CN); Yunnan Huapu quantum Material Co., Ltd, Kunming (CN); GuangDong ROI Optoelectronics Technology Co., Ltd., Dongguan (CN); East China Normal University, Shanghai (CN); Chongqing Huapu Intelligent Equipment Co., Ltd., Chongqing (CN); Chongqing Huapu Quantum Technology Co., Ltd., Chongqing (CN)

( * ) Notice: Subject to any disclaimer, the term of this patent is extended or adjusted under 35 U.S.C. 154(b) by 654 days.

(21) Appl. No.: 18/314,332

(22) Filed: May 9, 2023

(65) Prior Publication Data

US 2023/0364558 A1 Nov. 16, 2023

(30) Foreign Application Priority Data

May 10, 2022 (CN) ......................... 202210504006.7

(51) Int. Cl.
*B01D 53/88* (2006.01)
*A01N 31/08* (2006.01)
(Continued)

(52) U.S. Cl.
CPC ........... *B01D 53/885* (2013.01); *A01N 31/08* (2013.01); *A01N 59/16* (2013.01); *A61L 9/22* (2013.01);
(Continued)

(58) Field of Classification Search
CPC .................................................... B01D 53/885
See application file for complete search history.

(56) References Cited

FOREIGN PATENT DOCUMENTS

CN 107115721 9/2017
CN 108014360 A * 5/2018 ......... B01D 53/8687
(Continued)

OTHER PUBLICATIONS

English Translation of Document Identification No. CN 108014360 A provided by the InnovationQ+ website ip.com: Changsha Wudao Ind Design Co LTD; A Kind of Air Purifying Preparation Containing Catalyst; May 11, 2018 (Year: 2018).*
(Continued)

*Primary Examiner* — Kevin Joyner
(74) *Attorney, Agent, or Firm* — Hodgson Russ LLP

(57) ABSTRACT

A photocatalytic material includes activated carbon, titanium dioxide, zinc oxide, graphene, tourmaline powders, a nano-copper solution, carvacrol and deionized water. The
(Continued)

photocatalytic material is prepared by mixing the activated carbon, the titanium dioxide, the zinc oxide, the graphene, the tourmaline powders, the nano-copper solution, the carvacrol and the deionized water for a period ranging from 1 to 12 hours. A photocatalytic air screen filter for epidemic prevention includes a substrate and the photocatalytic material. The photocatalytic material is applied on a surface of the substrate, and the photocatalytic material is dried and cured. An amount of the material loaded on the surface of the substrate is in a range of 0.1 to 100 mg/cm$^2$.

14 Claims, 1 Drawing Sheet

(51) Int. Cl.

| | |
|---|---|
| ***A01N 59/16*** | (2006.01) |
| ***A61L 9/22*** | (2006.01) |
| ***B01D 46/00*** | (2022.01) |
| ***B01D 53/86*** | (2006.01) |
| ***B01J 21/06*** | (2006.01) |
| ***B01J 21/18*** | (2006.01) |
| ***B01J 35/39*** | (2024.01) |
| ***B01J 37/00*** | (2006.01) |
| ***F24F 8/167*** | (2021.01) |
| *B01J 35/45* | (2024.01) |

(52) U.S. Cl.
CPC ..... *B01D 46/0028* (2013.01); *B01D 53/8668* (2013.01); *B01D 53/8687* (2013.01); *B01J 21/063* (2013.01); *B01J 21/18* (2013.01); *B01J 35/39* (2024.01); *B01J 37/0036* (2013.01); *F24F 8/167* (2021.01); *B01D 2255/20707* (2013.01); *B01D 2255/702* (2013.01); *B01D 2255/802* (2013.01); *B01D 2257/708* (2013.01); *B01D 2257/91* (2013.01); *B01D 2259/4508* (2013.01); *B01D 2279/50* (2013.01); *B01J 35/45* (2024.01)

(56) References Cited

FOREIGN PATENT DOCUMENTS

| | | | | |
|---|---|---|---|---|
| CN | 109701515 | | 5/2019 | |
| CN | 110038513 | | 7/2019 | |
| TW | M553796 U | * | 1/2018 | |
| WO | WO-2019087883 A1 | * | 5/2019 | ............. A61K 31/05 |

OTHER PUBLICATIONS

English Translation of Document Identification No. WO 2019/087883 A1 provided by the InnovationQ+ website ip.com: Hiroki, Sugiura; Antiviral Composition, Anti-Norovirus Composition, Spray, Wiper; May 9, 2019 (Year: 2019).*

English Translation of Document Identification No. TW M553796 U provided by the InnovationQ+ website ip.com: Chen, Wen-Chi; Full-functional Fragrance Filter Screen; Jan. 1, 2018 (Year: 2018).*

CNIPA, First Office Action for CN Application No. 202210504006.7, Feb. 1, 2024.

* cited by examiner

PHOTOCATALYTIC MATERIAL, METHOD FOR PREPARING THE PHOTOCATALYTIC MATERIAL AND PHOTOCATALYTIC AIR SCREEN FILTER FOR EPIDEMIC PREVENTION

CROSS-REFERENCE TO RELATED APPLICATION

This application claims priority to Chinese Patent Application Serial No. 202210504006.7, filed May 10, 2022, the entire disclosure of which is incorporated herein by reference.

FIELD

The present disclosure relates to the field of air purification technology, particularly to a photocatalytic material, a method for preparing a photocatalytic material and a photocatalytic air screen filter for epidemic prevention.

BACKGROUND

With the development of the industrial society, air pollution becomes a serious problem. The pollutants in the indoor space include formaldehyde, hydrogen sulfide, ammonia, polluted organic matters, PM2.5 and other micro-particles. At present, the air purifier or fresh air system device is generally used to treat the pollutants in the indoor air. The main material of these air treatment devices is a filter element. A conventional air screen filter element is in the form of a combination of the activated carbon and the filter cotton. The adsorption of the activated carbon will be saturated, and thus the air screen filter materials need to be replaced regularly. Activation and regeneration of such materials are difficult, and the post-consumer materials will become new solid wastes.

SUMMARY

In a first aspect, embodiments of the present disclosure provide a photocatalytic material, including activated carbon, titanium dioxide, zinc oxide, graphene, tourmaline powders, a nano-copper solution, carvacrol and deionized water.

In a second aspect, embodiments of the present disclosure provide a method for preparing a photocatalytic material, including: mixing activated carbon, titanium dioxide, zinc oxide, graphene, tourmaline powders, a nano-copper solution, carvacrol and deionized water for a period ranging from 1 to 12 hours.

In a third aspect, embodiments of the present disclosure provide a photocatalytic air screen filter for epidemic prevention includes a substrate and the photocatalytic material as described in the first aspect. The photocatalytic material is applied on a surface of the substrate, and the photocatalytic material is dried and cured.

DETAILED DESCRIPTION

Figure 1:
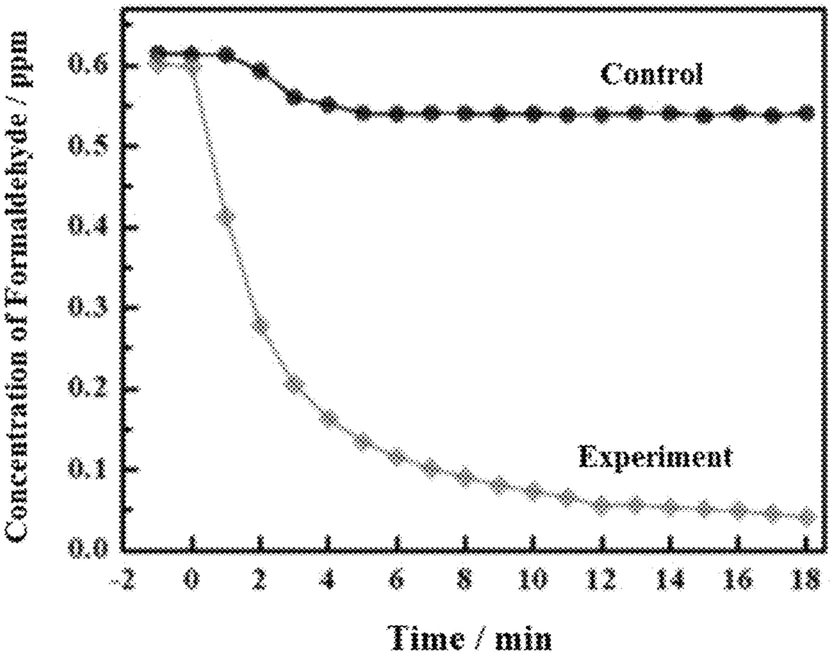
FIG. 1 is a graph showing results of formaldehyde decomposition by using a photocatalytic air screen filter for epidemic prevention of the present disclosure and a conventional air screen filter.

Description will be made below to the present disclosure with reference to accompanying drawings and embodiments.

In embodiments of the present disclosure, a photocatalytic material is provided, including activated carbon, titanium dioxide, zinc oxide, graphene, tourmaline powders, a nano-copper solution, carvacrol and deionized water.

In the photocatalytic material of the present disclosure, titanium dioxide is a photocatalytic component, zinc oxide is a component for antibacteria and disinfection, graphene is a component for improving photocatalysis, tourmaline powders are a component for generating negative oxygen ions, and carvacrol is a component for sterilization and disinfection. Titanium dioxide, zinc oxide and tourmaline powders are functional components for air purification. With illumination, titanium dioxide generates active substances such as superoxide free radicals, hydroxyl free radicals and electrons, which can efficiently decompose hazardous substances attached to the surface of the activated carbon. Zinc oxide is reacted with the moisture (i.e., water) in the air to generate zinc ions, which can realize a quick sterilization. Further, the sterilization performance may be improved by 3 to 5 times by a combination of the zinc oxide and carvacrol. Tourmaline powders can continuously generate negative oxygen ions. In the embodiments of the present disclosure, graphene and titanium dioxide are used as a visible light catalytic system, and zinc oxide and carvacrol are used as a disinfection and sterilization system. Therefore, based on the combination of the graphene-titanium dioxide system and the zinc oxide-carvacrol system, the photocatalytic material of the present disclosure can not only have the ability of decomposing the TVOC and formaldehyde for solving the problem that the existing air screen filter element (i.e., a core of the filter) needs to be replaced regularly due to the adsorption saturation and the short service life of the activated carbon, but also have the sterilization and disinfection function, which has not been provided by the existing air screen filter element. According to embodiments of the present disclosure, the hazardous substances on the surface of the activated carbon can be efficiently decomposed, so that the service life of the air screen filter element is greatly prolonged, and the functions of sterilization, disinfection and odor elimination for air can be comprehensively realized.

In some embodiments, a mass ratio of the activated carbon, the titanium dioxide, the zinc oxide, the graphene, the tourmaline powders, the nano-copper solution, the carvacrol and the deionized water is (1-100):(1-100):(1-100):(1-100):(1-100):(1-100):(1-1000).

In some embodiments, the activated carbon includes bamboo charcoal, coconut shell activated carbon, and coke carbon.

In some embodiments, the activated carbon has a specific surface area greater than $m^2/g$ and a size of 1 to 3 μm.

In embodiments of the present disclosure, a method for preparing a photocatalytic material is provided, including: mixing activated carbon, titanium dioxide, zinc oxide, graphene, tourmaline powders, a nano-copper solution, carvacrol and deionized water for a period ranging from 1 to 12 hours.

In this way, the uniformity and stability of the photocatalytic materials can be improved by fully mixing all the components of the photocatalytic material for 1 to 12 hours.

In some embodiments, the activated carbon, the titanium dioxide, the zinc oxide, the graphene, the tourmaline powder, the nano-copper solution, the carvacrol and the deionized water are mixed by using a ball mill.

In this way, the ball mill can grind a large-sized substances into small-sized particles during mixing, thereby improving the uniformity of the material during the mixing.

In embodiments of the present disclosure, a photocatalytic air screen filter for epidemic prevention is provided. The filter includes a substrate and the photocatalytic material as described above. The photocatalytic material is applied to or coated on a surface of the substrate. The photocatalytic material is dried and cured.

In this way, the photocatalytic material is distributed uniformly on the surface of the substrate, so that different positions of the prepared photocatalytic air screen filter for epidemic prevention have the same performance. The photocatalytic material is dried and cured to improve the stability of the photocatalytic material attached to the surface of the substrate, thereby improving the reliability of the performance of the prepared photocatalytic air screen filter for epidemic prevention for a long time.

In some embodiments, the substrate is made of a material selected from non-woven fabric, glass fiber, terylene cotton, nylon, polyester fiber or any combination thereof.

In some embodiments, the substrate is a screen or a gas-permeable membrane.

In some embodiments, the photocatalytic material is applied to the surface of the substrate with an adhesive.

In some embodiments, the adhesive may be a polyacrylic ester solution.

In this way, the photocatalytic material is attached to the surface of the substrate by using the adhesive, so that the adhesiveness of the photocatalytic material is stable and the process for applying the adhesive is simple.

In some embodiments, the photocatalytic material and the adhesive are mixed in a mass ratio of 1:10 to obtain a mixture and the mixture is applied to the surface of the substrate.

In this way, the photocatalytic material and the adhesive are mixed in a mass ratio of 1:10 and then attached to the surface of the substrate, so that the stability of the adhesiveness of the photocatalytic material is improved.

In some embodiments, the photocatalytic material is dried and cured by placing the photocatalytic material into a vacuum drying oven for drying at a drying temperature ranging from 50 to 60° C. for a drying period ranging from 2 to 6 hours.

In some embodiments, the photocatalytic material and the adhesive are mixed and attached to the surface of the substrate by uniformly spraying a mixed solution of the photocatalytic material and the adhesive on the surface of the substrate by electrospinning or nanospraying, or dipping the substrate in the mixed solution of the photocatalytic material and the adhesive.

Further, an amount of the material loaded on the surface of the substrate is in a range of 0.1 to 100 mg/cm2.

The photocatalytic material of the present disclosure has the functions of decomposition of full spectrum TVOCs and formaldehyde, sterilization and disinfection, mildew prevention, odor elimination and negative oxygen ion release.

In the present disclosure, the photocatalytic material includes the activated carbon, the titanium dioxide, the zinc oxide, the graphene, the tourmaline powders, the nano-copper solution, the carvacrol and deionized water. The titanium dioxide generates, under illumination, active substances such as superoxide free radicals, hydroxyl free radicals and electrons, which can efficiently decompose hazardous substances attached to the surface of the activated carbon. The zinc oxide is reacted with the moisture in the air to generate zinc ions, which can realize a quick sterilization. The sterilization performance may be improved by 3 to 5 times by a combination of the zinc oxide and carvacrol. The tourmaline powders can continuously generate negative oxygen ions. Based on the combination of these components, the problems of the existing air screen filter elements, such as the short service life, the single function of air purification and the need for regular replacement, can be solved. Meanwhile, with the material and the filter of the present disclosure, the indoor TVOCs and formaldehyde can be decomposed quickly and the unpleasant odor can be eliminated, germs and molds adsorbed on the surface of the activated carbon can be sterilized for all the time, and the negative oxygen ions beneficial to physical and mental health are continuously released.

FIG. 1 is a graph showing formaldehyde decomposition results of a photocatalytic air screen filter for epidemic prevention of the present disclosure (Experiment) and a conventional air screen filter (Control). It can be seen from FIG. 1 that when the photocatalytic air screen filter for epidemic prevention of the present disclosure is used for the decomposition of formaldehyde, the concentration of formaldehyde decreased rapidly with increase of time. When the conventional air screen filter is used for the decomposition of formaldehyde, the concentration of formaldehyde changes a little and remains at a high level even after a certain period of time. Therefore, compared with the conventional air screen filter, the photocatalytic air screen filter for epidemic prevention of the present disclosure has a better formaldehyde decomposition performance.

Figure 2:
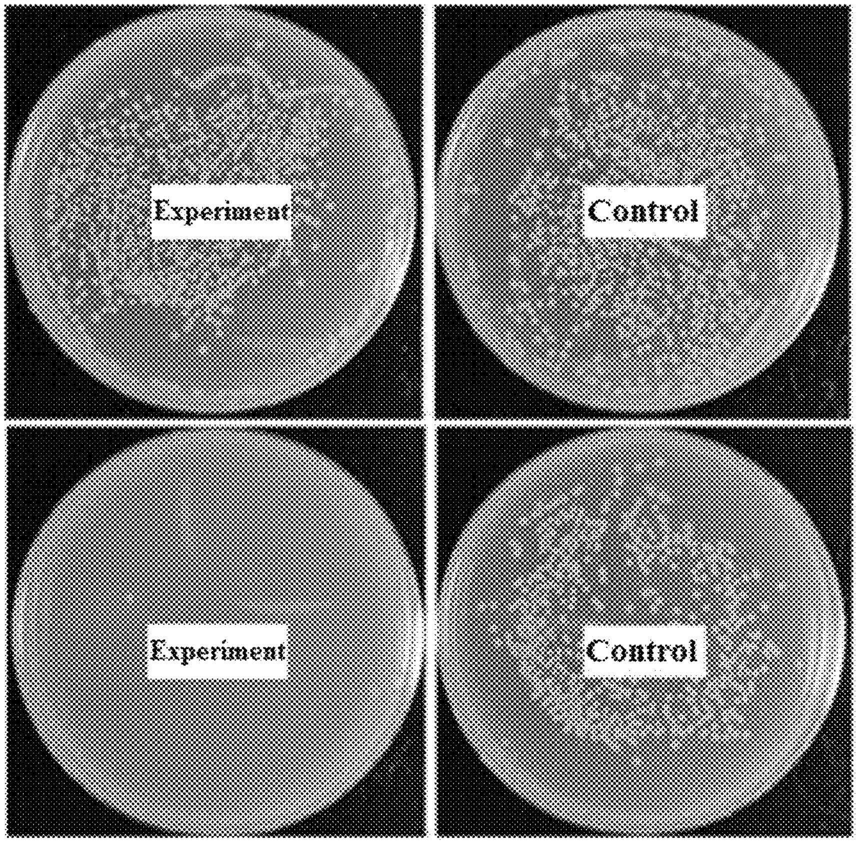
FIG. 2 shows pictures of results of an antibacterial activity test performed on a photocatalytic air screen filter for epidemic prevention of the present disclosure and a conventional air screen filter.

FIG. 2 shows the antibacterial activity by the photocatalytic air screen filter for epidemic prevention (Experiment) of the present disclosure as compared to that of a conventional air screen filter (Control). From FIG. 2, it is clear that, in the test of the photocatalytic air screen filter for the antibacterial activity, almost 95% or above of the antibacterial effect was achieved by the treatment of the photocatalytic air screen filter after a certain time period; while 50% or less of the antibacterial effect was achieved by the treatment of the conventional air screen filter for the same time period. Therefore, the photocatalytic air screen filter of the present disclosure exhibits much superior antibacterial effect.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A photocatalytic material, comprising activated carbon, titanium dioxide, zinc oxide, graphene, tourmaline powders, a nano-copper solution, carvacrol and deionized water, wherein the activated carbon includes bamboo charcoal, coconut shell activated carbon, and coke carbon.

2. The photocatalytic material of claim 1, wherein a mass ratio of the activated carbon to the deionized water is 1-100, a mass ratio of the titanium dioxide to the deionized water is 1-100, a mass ratio of the zinc oxide to the deionized water is 1-100, a mass ratio of the graphene to the deionized water is 1-100, a mass ratio of the tourmaline powders to the deionized water is 1-100, a mass ratio of the nano-copper solution to the deionized water is 1-100, and a mass ratio of the carvacrol to the deionized water is 1-1000.

3. The photocatalytic material of claim 1, wherein the activated carbon has a specific surface area greater than 500 $m^2/g$ and a particle size of 1 to 3 μm.

4. A method for preparing the photocatalytic material of claim 1, wherein the activated carbon, the titanium dioxide, the zinc oxide, the graphene, the tourmaline powders, the nano-copper solution, the carvacrol and the deionized water are mixed for a period ranging from 1 to 12 hours.

5. The method of claim 4, wherein the activated carbon, the titanium dioxide, the zinc oxide, the graphene, the tourmaline powders, the nano-copper solution, the carvacrol and the deionized water are mixed by using a ball mill.

6. A photocatalytic air screen filter for epidemic prevention, comprising a substrate and the photocatalytic material of claim 1, wherein the photocatalytic material is applied on a surface of the substrate, and the photocatalytic material is dried and cured.

7. The photocatalytic air screen filter of claim 6, wherein the photocatalytic material is applied to the surface of the substrate by using an adhesive.

8. The photocatalytic air screen filter of claim 7, wherein the photocatalytic material and the adhesive are mixed in a mass ratio of 1:10 to obtain a mixture and the mixture is applied to the surface of the substrate.

9. The photocatalytic air screen filter of claim 6, wherein the photocatalytic material is dried and cured by placing the photocatalytic material into a vacuum drying oven for drying at a drying temperature ranging from 50 to 60° C. for a drying period ranging from 2 to 6 hours.

10. The photocatalytic air screen filter of claim 8, wherein a mixed solution of the photocatalytic material and the adhesive is applied on the surface of the substrate by electrospinning or nanospraying.

11. The photocatalytic air screen filter of claim 8, wherein the substrate is immersed in a mixed solution of the photocatalytic material and the adhesive.

12. The photocatalytic air screen filter of claim 8, wherein an amount of the photocatalytic material and the adhesive loaded on the surface of the substrate is in a range of 0.1 to 100 $mg/cm^2$.

13. The photocatalytic air screen filter of claim 8, wherein the adhesive is a polyacrylic ester solution.

14. The photocatalytic air screen filter of claim 6, wherein the substrate is made of a material selected from non-woven fabric, glass fiber, terylene cotton, nylon, polyester fiber or any combination thereof.

* * * * *